United States Patent
Shinoki et al.

(12)
(10) Patent No.: US 6,872,577 B2
(45) Date of Patent: Mar. 29, 2005

(54) AGGLUTINATION ASSAY METHOD AND ELEMENT IN DRY SYSTEM

(75) Inventors: Hiroshi Shinoki, Saitama (JP); Yoshikazu Amano, Saitama (JP)

(73) Assignee: Fuji Photo Film Co., Ltd., Kanagawa (JP)

(*) Notice: Subject to any disclaimer, the term of this patent is extended or adjusted under 35 U.S.C. 154(b) by 392 days.

(21) Appl. No.: 10/021,759

(22) Filed: Oct. 22, 2001

(65) Prior Publication Data

US 2002/0055188 A1 May 9, 2002

Related U.S. Application Data

(62) Division of application No. 09/493,574, filed on Jan. 28, 2000.

(30) Foreign Application Priority Data

Jan. 28, 1999 (JP) .............................................. 11-20088

(51) Int. Cl.$^7$ ............................................. G01N 33/543
(52) U.S. Cl. ........................ 436/518; 436/523; 436/534; 436/535
(58) Field of Search ................................ 436/514, 518, 436/523, 524, 525, 526, 527, 528, 529, 530, 531, 532, 533, 534, 535, 543, 544, 546; 435/4, 7.1, 7.2, 7.92, 7.93, 7.94, 7.95

(56) References Cited

U.S. PATENT DOCUMENTS

| | | | | |
|---|---|---|---|---|
| 4,620,977 A | * | 11/1986 | Strahilevitz | 424/193.1 |
| 4,753,873 A | * | 6/1988 | Beltz et al. | 435/5 |
| 5,547,848 A | * | 8/1996 | Shinoki et al. | 435/7.9 |
| 6,174,700 B1 | * | 1/2001 | Haynes et al. | 435/68.1 |
| 6,485,703 B1 | * | 11/2002 | Cote et al. | 424/9.1 |

* cited by examiner

*Primary Examiner*—Christopher I. Chin
*Assistant Examiner*—Ann Y. Lam
(74) *Attorney, Agent, or Firm*—Reed Smith LLP

(57) ABSTRACT

An agglutination assay method for quantitatively determination of an analyte in a liquid sample using particles bearing an anti-analyte. A non-fluid substance which retains the particles while suppressing the diffusion of the particles therein is used as a medium which is to be a place where the agglutination of the particles takes place. Upon analysis, a solation agent is added to the non-fluid substance medium to increase the fluidity of the non-fluid substance, thereby the particles bearing the anti-analyte can diffuse in the medium to cause the agglutination with the analyte. Preferably, the solation agent is added to the non-fluid medium together with the sample. The non-fluid substance medium containing the particle-labeled anti-analyte can be stored with a higher stability in the dry state. A dry analysis element for enabling such analysis method is also provided.

11 Claims, 1 Drawing Sheet

AGGLUTINATION ASSAY METHOD AND ELEMENT IN DRY SYSTEM

The is a division of application Ser. No. 09/493,574, filed Jan. 28, 2000, which claims the priority of Japanese Application No. 11-20088 filed Jan. 28, 1999, the complete disclosure of which is hereby incorporated by reference.

BACKGROUND OF THE INVENTION

1. Field of the Invention

The present invention relates to a method for detecting and analyzing a trace substance by utilizing the agglutination assay, in which an analyte reacts with a particle-labeled anti-analyte, such as an antibody, to cause the particle agglutination. Particularly, the present invention relates to a dry analysis method for determining an analyte, which comprises bringing a solation agent into contact with a medium of a non-fluid substance to increase the fluidity of the medium, thereby causing the agglutination of the particles bearing the anti-analyte in the medium. Also, the present invention relates to a dry analysis element which enables such analysis method.

2. Description of the Related Art

In recent years, it has come to be very important to quantitatively analyze a trace substance, particularly antibody or antigen, in a specimen promptly, conveniently and precisely in order to diagnose the condition of diseases or judge the effects of treatment. For this purpose, widely employed has been an immuno-serological test for assaying the existence of an antigen or antibody in the body fluid, in which the antibody or antigen is adsorbed and immobilized to insoluble carrier particles and the resulting particles is reacted with the antigen or antibody.

The latex particles agglutination immunoassay is performed routinely by mixing a suspension of antibody-coated latex particles (sensitized latex) with a specimen on a glass plate. The latex particles agglutinate, or fail to agglutinate, as a result of interacting with the analyte antigen in the specimen. The extent of the agglutination can be determined by visual inspection. This assay makes it possible to semi-quantitatively analyze the antigen in the specimen by diluting the specimen at various ratios similar to another qualitative assay.

In Japanese Patent Publication Nos. 11575/1983, 43138/1987 and 55013/1987, there is proposed a method, in which latex particles having an antibody bound thereto is reacted with the antigen in the sample and the amount of the agglutination of the latex particles is determined optically by nephelometry. According to the proposed method, an antigen or antibody has come to be analyzed quantitatively by an automatic analyzer.

In addition, Unexamined Japanese Patent Publication (KOKAI) Nos. 141665/1990 and 209879/1993 disclose a method wherein an antigenic substance is detected by measuring a change in the absorbance upon the agglutination of the colloidal gold-labeled antibodies.

The above-described immunoassays do not need B/F separation and in this point, they are useful. The latex reagent is, however, poor in storage stability, since it is in the liquid form. In the colloidal gold agglutination, the colloidal gold solution or dispersion is not suitable as a reagent because of poor storage stability. A colloidal gold-labeled reagent in the lyophilized form must be mixed with a dedicated solution upon measurement, which makes the operation cumbersome. This method is also accompanied with such a drawback as unsuitability for use in the measurement of a small amount of a sample.

A so-called dry analysis method is, on the other hand, superior in storage stability and convenient operation. The so-called wet system (or solution system) comprises dissolving a reagent to be used for the assay in an aqueous solvent, thereby preparing the corresponding reagent solution, adding this reagent solution to a sample to be analyzed and then measuring the color reaction product by a calorimeter, while the dry analysis method comprises spotting an aqueous sample directly to a dry analysis element, such as test piece, analytical slide or analytical tape, having a reagent composition incorporated therein in the dry form and effecting colorimetry of the color development or color change occurring in the element. The dry system is superior to the wet system using a reagent solution in convenient operation and speedy assay.

A method for causing agglutination in the layer of a dry analysis element, thereby directly detecting the existence of an agglutinate itself in the layer construction has not yet been proposed. It can adopt the agglutination in a gel state, like as the Ouchterlony technique, which involving immunoprecipitation through an agar gel. Ouchterlony test is one of immunodiffusion methods, in which an antigen and an antiserum diffuse in the agar gel from each of two holes made in the gel plate. The antigen and the antiserum meet each other to form a visible precipitation line. Long time duration is necessary for the test, since the diffusion lasts for some time.

In order to cause agglutination of the labeling carrier in a gel medium in short time, the gel which is to be a place for reaction is required to have fluidity sufficient for causing agglutination. If sufficient humidity is required for maintaining this fluidity, such an analysis element cannot be classified as an element stored in a dry condition (or semi-dry condition). Moreover, when the gel has high fluidity, it needs a special care for packaging or storage, which makes this method far from convenience.

SUMMARY OF THE INVENTION

The present invention has been accomplished in view of the aforementioned circumstances, and a first object of the present invention is to provide a dry analysis method for determining an analyte using an agglutination of the particles bearing an anti-analyte, by which a highly sensitive analysis is ensured while using a simple operation and a reagent can be stored with a higher stability in the dry state.

A second object of the present invention is to provide a dry analysis element which can detect agglutination caused by the reaction between an analyte and an anti-analyte labeled with labeling particle, thereby analyzing the analyte in a convenient and highly sensitive manner.

The first object of the present invention is attained by an agglutination assay method for quantitatively determination of an analyte in an aqueous liquid sample using particles bearing an anti-analyte, the anti-analyte being capable of specifically binding to the analyte so as to cause agglutination of the particles, comprising:

providing a mixture of said particles and a non-fluid substance which retains said particles while suppressing the diffusion of said particles;

contacting said mixture with a solating agent for increasing the fluidity of the non-fluid substance in said mixture;

contacting the sample with said mixture to cause the agglutination of the particles in said mixture; and measuring the extent of the agglutination of the particles to determine the amount of the analyte in the sample.

In the invention, a non-fluid substance is used as a medium which is to be a place for the agglutination of the labeling carrier or particle bearing an anti-analyte. Upon analysis, the fluidity of the medium is enhanced by the solation agent. In other words, diffusion properties of the labeling particle is enhanced, and accordingly the diffusion and agglutination of the labeling particles is accelerated. By mixing the labeling carrier or particle with the non-fluid substance to form a medium, the medium is, upon storage, dry enough not to impair the stability of a reagent composition to be employed. While upon analysis, the medium is solated and liquefied by the solation agent and has acquired fluidity sufficient for causing agglutination of the labeling particles.

In a preferred embodiment, a solation agent is added to an aqueous liquid sample containing an analyte and then, a non-fluid medium containing a particle-labeled anti-analyte is brought into contact with the resulting mixture. In case where this medium is formed in a membrane or film form, the agglutinate formed in the medium can easily be detected by measuring an optical change of the transmitted or reflected light from outside of the film-like medium. The existence of the agglutinate and its amount may be detected as a turbidity change in the film-like medium or as a change in the color tone of the labeling particle due to agglutination.

The second object of the present invention is attained by a dry analysis element for quantitatively determining an analyte in an aqueous liquid sample by measuring the extent of agglutination of particles bearing an anti-analyte, the anti-analyte being capable of specific binding to the analyte to cause the agglutination of said particles, comprising:

a non-fluid medium layer composed of a non-fluid substance which retains said particles bearing the anti-analyte therein while suppressing the diffusion of said particles; and a water permeable layer which is superimposed on said non-fluid medium layer and contains a solation agent being capable to increasing the fluidity of the non-fluid substance;

whereby, when the sample is applied to the water permeable layer, said solation agent transfers to the non-fluid medium layer from the water permeable layer together with the sample and increases the fluidity of said non-fluid substance to cause the agglutination of the particles in the non-fluid medium layer.

In the second aspect of the present invention, the non-fluid medium layer is used as a field where the agglutination takes place. Upon analysis, the solating agent migrates from the upper water permeable layer to the lower non-fluid medium layer together with liquid sample applied to the element. The solating agent solates or liquefys the non-fluid substance of the non-fluid medium layer to enhance the diffusion of the particles and thereby the agglutination of the particles is accelerated. This constitution makes it possible to store the element under dry conditions sufficient for not damaging the stability of a reagent composition to be employed. Upon analysis, the non-fluid substance is solated and liqufied by the action of the solating agent, thereby maintaining fluidity sufficient for causing agglutination of the labeling particles.

DETAILED DESCRIPTION OF THE INVENTION

Analyte and Anti-Analyte

Figure 1:
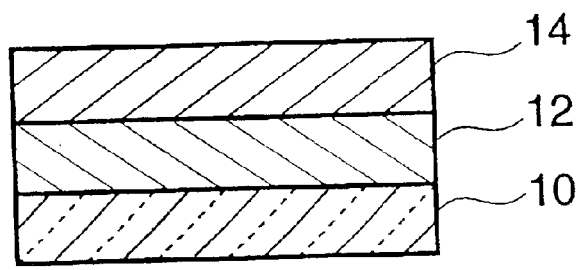
FIG. 1 is an illustration showing the layer structure of one embodiment of the dry analysis element according to the present invention.

As an analyte or a substance to be analyzed in the present invention, any substance can be used insofar as there exists a specific binding partner or substance thereto in the nature or such a substance can be prepared by chemical means. The anti-analyte, i.e., specific binding partner or substance as used herein means a substance which can specifically recognizes and binds to the analyte and at the same time, can be bound to a labeling carrier particle.

Examples of the combination of an analyte and an anti-analyte thereto include combinations of antigen and antibody, a certain saccharide and lectin, biotin or avidin, protein A and IgG, hormone and receptor thereof, enzyme and substrate, and nucleic acid and complementary nucleic acid. In the above-exemplified combinations, the analyte and the anti-analyte may be reversed.

The most ordinary example is a combination of an antigen as an analyte and an antibody as an anti-analyte. The antibody as an anti-analyte may be either a polyclonal or monoclonal antibody. Alternatively, a plurality of different antibodies can be used. No particular limitation is imposed on the class of the antibody and it does not matter whether it is IgG or IgM. It may be a fragment of an antibody, for example, Fab, Fab' or $F(ab')_2$. When a monoclonal antibody is employed as a specific binding substance, an analyte antigen must have at least two same epitopes in order to cause agglutination of a labeling particle having an antibody bound thereon. Alternatively, at least two different antibodies which binds to different epitopes of the analyte antigen, respectively, may be bound to the labeling carrier particle. When the analyte antigen is composed of plural sub-units, such as hemoglobin, however, there is no need to use plural different monoclonal antibodies. Binding plural molecules of single kind of monoclonal antibody to the labeling carrier (particle), the agglutination of the particles can be caused by the reaction with the analyte antigen.

Labeling Particle

As a labeling carrier or particle for labeling by binding an anti-analyte, any particle can be used insofar as it undergoes agglutination as a result of reaction with the analyte and the anti-analyte bound to the particle and the degree of the agglutination falls within an detectable range. As the labeling particle, those ordinarily employed for immuno-agglutination can be used. Examples of the carrier particle include organic high-molecular latex particles such as polystyrene and styrene-butadiene copolymer and metals such as colloidal metal. The labeling particles (or colloid) are preferred to have an average particle size falling within a range of 0.02 to 10 $\mu$m. When the particles have an excessively large particle size, optical strength due to optical reflection or light scattering of the particle itself prior to the immunoreaction becomes too high, resulting in difficulty in measurement. Too small particle sizes, on the other hand, tend to lower the detection sensitivity of the agglutinate.

Any conventionally known colloidal metal can be used as a labeling particle. Examples include colloidal gold, colloidal silver, colloidal platinum, colloidal iron and colloidal aluminum hydroxide. In particular, colloidal gold and colloidal silver are preferred because they assume red and yellow colors, respectively at a proper particle size.

The particle size of a colloidal metal is preferably about 1 to 500 nm. The size of 5 to 100 nm is particularly preferred, because it permits development of a strong color tone. The colloidal metal and the anti-analyte can be bound in a conventionally known manner (for example, The Journal of Histochemistry and Cytochemistry, 30(7), 691–696 (1982)).

Non-Fluid Substance (Medium)

A medium for retaining a labeling particle having an anti-analyte bound thereto is a substance lacking in fluidity by itself but has heightened fluidity by the addition of a solation agent, which will be described later, thereby causing agglutination of the labeling particles. Even in the absence of the solation agent, however, it does not need to be free from fluidity in an extent completely suppressing diffusion of the labeling particle and not causing agglutination. Even when the labeling particles are dispersed and retained in a liquid-state dispersion medium, if the diffusion of the labeling particles are accelerated thereby causing agglutination, any medium can be used as a non-fluid medium in the invention. In short, the term "a non-fluid medium" as used herein means a medium capable of retaining the labeling particles but suppressing the diffusion of the labeling particles when a solation agent is not acted on the medium compared with when a solation agent is acted.

As the non-fluid substance (medium), a gel may also be used for example. The gel generally has a net structure formed of linear molecular colloids interlocked by crosslinking and is solidified in a jelly form. It is presumed that if the gel has a high water content, labeling carrier particles tend to be diffused through water filling the interspace of the net structure and the dispersion medium, and therefore agglutination occurs to some extent. Even in this case, diffusion and agglutination of the labeling particle can be accelerated by solation of the gel medium. Since a soft gel having a high water content is poor in storage stability and needs care upon handling, it is not suited for use in the dry analysis method requiring convenience and stability.

In a preferred embodiment, an insoluble starch derivative such as carboxymethylated starch may be used as a non-fluid substance (medium) when α-amylase is used as a solation agent. The starch derivative is excellent because it permits uniform dispersion and retention of a labeling particle and easy formation of the membrane.

Solation Agent (Fluidizing Agent)

By the addition of a solation agent, a non-fluid substance which serves as a medium for retaining a labeling particle bearing an anti-analyte thereon has increased fluidity and causes agglutination of the labeling particles. The solation agent does not necessarily solate or liquefy the non-fluid substance completely. It is sufficient that agglutination of the labeling particle is more brisk in the presence of the solation agent than in the absence of it. It is rather convenient for dry analysis that the non-fluid medium added with a solation agent can maintain some extent of non-fluidity or hardness enough for maintaining its own shape. The term "solation agent" as used herein means an agent which provides the non-fluid substance (medium) with an agglutination-accelerating environment such that the diffusion properties of the labeling particle dispersed and retained in the medium is increased, thereby tending to cause or accelerate agglutination.

Examples of the means for solating a non-fluid medium include enzymatic hydrolysis, decomposition of a substance due to pH change and photo-decomposition by laser or the like.

Solation by enzymatic hydrolysis is particularly preferred, because this hydrolysis proceeds under mild conditions. When a polysaccharide such as oligosaccharide, starch derivative or starch decomposition product is used as a non-fluid substance (medium), a glucosidase such as amylase which hydrolyses such a polysaccharide, thereby destroying its crosslinking structure can be used as a solation agent.

Another examples of the combination of a non-fluid substance (medium) and solation agent include that of a cellulose derivative and cellulase, pullulan and pullnase, gelatin and a peptidolytic enzyme such as pepsin, and nucleic acid and nuclease. Among them, the combination of an insoluble starch derivative such as carboxymethylated starch and α-amylase is excellent.

Analysis Method

An aqueous liquid sample containing an analyte is brought into contact with the film of a non-fluid medium in which particle-labeled anti-analyte has been dispersed and retained. Simultaneously with or prior to the contact, a solation agent is brought into contact with the film, thereby heightening the fluidity of the non-fluid medium and providing a place where the agglutination takes place. It is also possible to mix a solation agent with an aqueous sample in advance and then bring the resulting mixture into contact with the film of the non-fluid medium. That is, the solation agent may be supplied to the non-fluid medium, together with the analyte. Alternatively, a water permeable layer having a solation agent incorporated therein may be superimposed on the non-fluid medium film. In this case, the solation agent can be transferred together with the analyte to the non-fluid medium film by spotting the aqueous liquid sample on the water permeable layer.

The existence and degree of agglutination in the non-fluid medium film may be detected as an optical change of a transmitted or reflected light from the outside of the film, may be detected as a turbidity change in the film medium, or may be detected by a change in the color tone of the labeling particle owing to agglutination.

Layer Structure of Dry Analysis Element

FIG. 1 shows an embodiment of the dry analysis element according to the invention. In FIG. 1, reference numeral 10 designates a support on which a non-fluid medium layer (film layer) 12, and a water permeable layer 14 containing a solation agent are laminated.

The support 10 may be light non-transmitting (opaque), light-semi-transmitting (translucent), or light-transmitting (transparent), and it is generally preferable that the support is light-transmitting and water impermeable. Polyethylene terephthalate, polystyrene or the like is preferably employed as a material for the light-transmitting and water impermeable support.

As described above, the non-fluid medium layer 12 is composed of a non-fluid medium which retain the particle-labeled anti-analyte while suppressing the diffusion of the particle as compared with the case where it is solated.

In the non-fluid medium layer, a buffer may be incorporated so that the specific binding reaction between the particle-labeled anti-analyte and the analyte occurs at an optimum pH. For the antigen-antibody reaction, for example, pH buffers usable for ordinary antigen-antibody reaction can be employed. Specific examples of usable buffers are buffer reagents containing tris(hydroxymethyl)aminomethane (Tris), buffer reagents containing phosphate, buffer reagents containing borate, buffer reagents containing citric acid or citrate, buffer reagents containing glycine, buffer reagents containing Bicine, buffer reagents containing HEPES, and buffer reagents containing Good's buffer agent such as MES (2-morpholinoethanesulfonic acid). The reaction may be effected at any pH insofar as the pH is within a range permitting ordinary antigen-antibody reaction.

In the non-fluid medium layer (film), a high molecular polymer such as polyvinyl alcohol, polyvinyl pyrrolidone or PEG (polyethylene glycol) may be incorporated for the purpose of promoting agglutination.

The water permeable layer 14 contains a solation agent. In order to ensure water permeability of the layer, the water permeable layer is preferably a porous layer composed of a porous medium or a layer made of a hydrophilic polymer binder.

The porous layer may be fibrous or non-fibrous. As the fibrous material, filter paper, non-woven cloth, woven cloth (e.g., plain woven cloth), knitted cloth (e.g., tricot knitted cloth) or filter paper made of glass fibers may be used. Examples of the non-fibrous material may be either one of a membrane filter composed of cellulose acetate as described in Unexamined Japanese Patent Publication No. 53888/1974 (corresponding to U.S. Pat. No. 3,992,258), or a particulate structure layer containing interconnected voids and composed of inorganic or organic fine particles as disclosed in Unexamined Japanese Patent Publication Nos. 53888/1974 (corresponding to U.S. Pat. No. 3,992,258), 90859/1980 (corresponding to U.S. Pat. No. 4,258,001) and 70163/1983 (corresponding to U.S. Pat. No. 4,486,537). A laminated structure made of partially bonded multiple porous layers may also be preferably used, examples of such structure being disclosed in Unexamined Japanese Patent Publication Nos. 4959/1986 (corresponding to EP 0166365A), 116248/1987, 138756/1987 (corresponding to EP 0226465A), 138757/1987 (corresponding to EP 0226465A) and 138758/1987 (corresponding to EP 0226465A).

The porous layer may be a spreading layer having a so-called metering function to spread a liquid over an area substantially in proportion to the volume of the liquid fed thereto. Preferable materials for the spreading layer are woven and knitted fabrics. The woven fabrics or like may be subjected to the glow discharge treatment as described in Unexamined Japanese Patent Publication No. 663599/1982 (corresponding to U.S. Pat. No. 4,783,315 and GB 2,087, 974A). In order to adjust the area or rate for spreading, the spreading layer may contain a hydrophilic polymer or a surfactant as described in Unexamined Japanese Patent Publication Nos. 222770/1985 (corresponding to EP 0162301A), 219397/1988 (corresponding to DE 37 17 913A), 112999/1988 (corresponding to DE 37 17 913A) and 182652/1987 (corresponding to DE 37 17 913A).

Preparation of Dry Analysis Element

The dry analysis element of the invention may be prepared by any of the known processes described in the specifications of the aforequoted patents. The analysis element of the invention may be cut into a square piece having sides each ranging from about 15 to 30 mm or a disk having a substantially same area. It is preferred, in view of the preparation, packaging, shipping, storage and measuring operations, that the element be contained in a slide frame as descried, for example, in Japanese Patent Publication No. 28331/1982 (corresponding to U.S. Pat. No. 4,169,751), Unexamined Japanese Utility Model Publication No. 142454/1981 (corresponding to U.S. Pat. No. 4,837,990), Unexamined Japanese Patent Publication No. 63452/1982, Unexamined Japanese Utility Model Publication No. 32350/1983 and Unexamined Japanese Patent Publication No. 501144/1983 (corresponding to International Publication WO 83/00391) for use as a slide for chemical analysis. For the convenience in some uses, it may be formed in a long tape shape which is contained in a cassette or magazine, or a small piece thereof may be applied on or contained in a card having an opening.

Analysis Method Using the Dry Analysis Element

The analysis element of the invention may be used for the quantitative analysis of an analyte in a sample liquid by using it through the operations described in the specifications of the aforequoted patents. When the analyte is an antigen or an antibody, about 5 $\mu$L to about 30 $\mu$L, preferably 8 $\mu$L to 15 $\mu$L, of an aqueous sample liquid such as plasma, serum or urine is spotted on the water permeable layer 14. The analysis element thus spotted is then incubated at a constant temperature of from about 20° C. to about 45° C., preferably at a constant temperature of from about 30° C. to about 40° C., for 1 to 10 minutes. The reflection optical density of the color or the change in color in the element may be measured from the light-transmitting support side, and the quantity of the analyte contained in the sample can be determined using a preliminarily prepared calibration curve based on the principle of colorimetry. The volume of the spotted liquid sample and the time and temperature for incubation are maintained constant to improve the accuracy in quantitative analysis.

The measuring operation may be carried out while using the chemical analysis apparatuses described in Unexamined Japanese Patent Publication Nos. 125543/1985, 220862/1985, 294367/1986 and 161867/1983 (corresponding to U.S. Pat. No. 4,424,191) to realize quantitative analysis at a high accuracy by extremely easy operation. Depending on the purpose or required precision, however, semi-quantitative measurement may be conducted by visually judging the degree of color development.

When the analysis element has no water permeable layer 14, that is, a solation agent is not incorporated in the analysis element, an aqueous sample liquid may be mixed with a solation agent outside the analysis element followed by spotting on a non-fluid medium layer.

For example, when an antigen, an antibody, a colloidal metal, carboxymethylated starch and amylase are used as an analyte, an anti-analyte, a labeling carrier particle, a non-fluid medium and a solation agent, respectively, preparation of a dry analysis element and dry analysis using the element can be carried out as described below.

Specifically, an antibody labeled with a colloidal metal is dispersed in a solution of carboxymethylated starch. The resulting dispersion is applied to a light-transmitting support 10, followed by drying, whereby a film 12 is formed. A cloth 14 impregnated with amylase is laminated onto the film, thereby a dry analysis element for agglutination assay can be prepared.

An aqueous liquid sample containing an analyte (i.g., antigen) is spotted and applied onto the resulting analysis element. The analyte transfers into the carboxymethylated starch layer 12, together with the amylase contained in the cloth 14 to cause the enzymatic hydrolysis of the carboxymethylated starch and the antigen-antibody binding reaction in this layer 12, resulting in agglutination of the colloidal metal.

Agglutination changes the color tone of the colloidal metal so that the analyte in the sample can be detected and quantitatively analyzed by measuring a change in the color tone of the gel. For example, a colloidal gold before agglutination assumes a reddish violet color having a main absorption wavelength at about 540 nm. By the agglutination, the colloidal gold increases in size, leading to shifting of its absorbance to the side of a longer wavelength, and as a result, assumes a pale reddish purple or gray color. Accordingly, the analyte (antigen) can be quantitatively analyzed from a decrease in the reflection optical density at 540 nm, an increase in the reflection optical density at about 630 nm which appears by agglutination, or a difference between reflection optical densities at 540 nm and 630 nm.

EXAMPLE 1

Preparation of Anti-Hemoglobin Antibody-Bound Colloidal Gold

To 600 μL of a colloidal gold solution (product of BRITISH BIOCELL) having a particle size of 50 nm was added 11 μL of a 0.2M potassium carbonate solution to adjust the pH to 9.0. To 611 μL of the resulting mixture was added 60 μL of an 0.1 mg/mL anti-hemoglobin antibody solution which was prepared by diluting 2.5 mg/mL anti-hemoglobin solution (product of MEDIX BIOCHEM, 0.02M phosphate buffer, 0.02% sodium azide, pH 6.4) with distilled water. After stirring, 600 μL of 10 mM phosphate buffer (pH 6.4, supplemented with 1% BSA (bovine serum albumin) and 0.05% sodium azide) was added as a stabilizer. The resulting mixture was centrifuged at 145,000 rpm for 60 minutes to remove the supernatant. The precipitate was collected and resuspended in 100 μL of 10 mM phosphate buffer (pH 6.4, 1% BSA, 0.05% sodium azide), whereby an anti-hemoglobin antibody-bound colloidal gold suspension was prepared.

EXAMPLE 2

Preparation of Slide (1) of Anti-Hemoglobin Antibody-Bound Colloidal Metal Film 50 mg of carboxymethylated starch was added to 2.5 μL of a solution containing 700 μg of the anti-hemoglobin antibody-bound colloidal gold (colloidal gold-labeled antibody) obtained in Example 1, followed by stirring. The resulting dispersion was coated onto a polyethylene terephthalate (PET) film, followed by drying under reduced pressure, whereby an anti-hemoglobin antibody-bound colloidal gold film (layer) was formed.

A cloth (5×5 cm: a tricot knitted cloth which had been knitted to 36 gauges by a PET spun yarn having fineness of 50 deniers and thickness of about 250 μm) was impregnated with 3 mL of 1 mg/mL α-amylase solution (10 mM glycerophosphate buffer, pH 7.0) and the resulting cloth was allowed to stand for 30 minutes. Then, the cloth was adhered onto the anti-hemoglobin antibody-bound colloidal metal film with a hot-melt adhesive, whereby a slide (1) of the anti-hemoglobin antibody-bound colloidal gold film was prepared. As a comparative example, a slide (2) was prepared in a similar manner to the above except that the cloth was not impregnated with α-amylase.

EXAMPLE 3

Hemoglobin (product of Exocell) was diluted with a PBS solution containing 0.05% polyethylene glycol to prepare a hemoglobin solution having a predetermined concentration. Onto the slides (1) and (2) of the anti-hemoglobin antibody-bound colloidal gold film, 10 μL portions of the diluted hemoglobin solution were spotted, followed by incubation at 37° C. for 6 minutes. Then, the reflection optical densities at central wavelengths of 550 nm and 630 nm were measured from the side of the PET support, respectively. The difference between the optical density $OD_{550}$ at 550 nm and that $OD_{630}$ at 630 nm was determined. The results are shown in FIG. 2.

Figure 2:
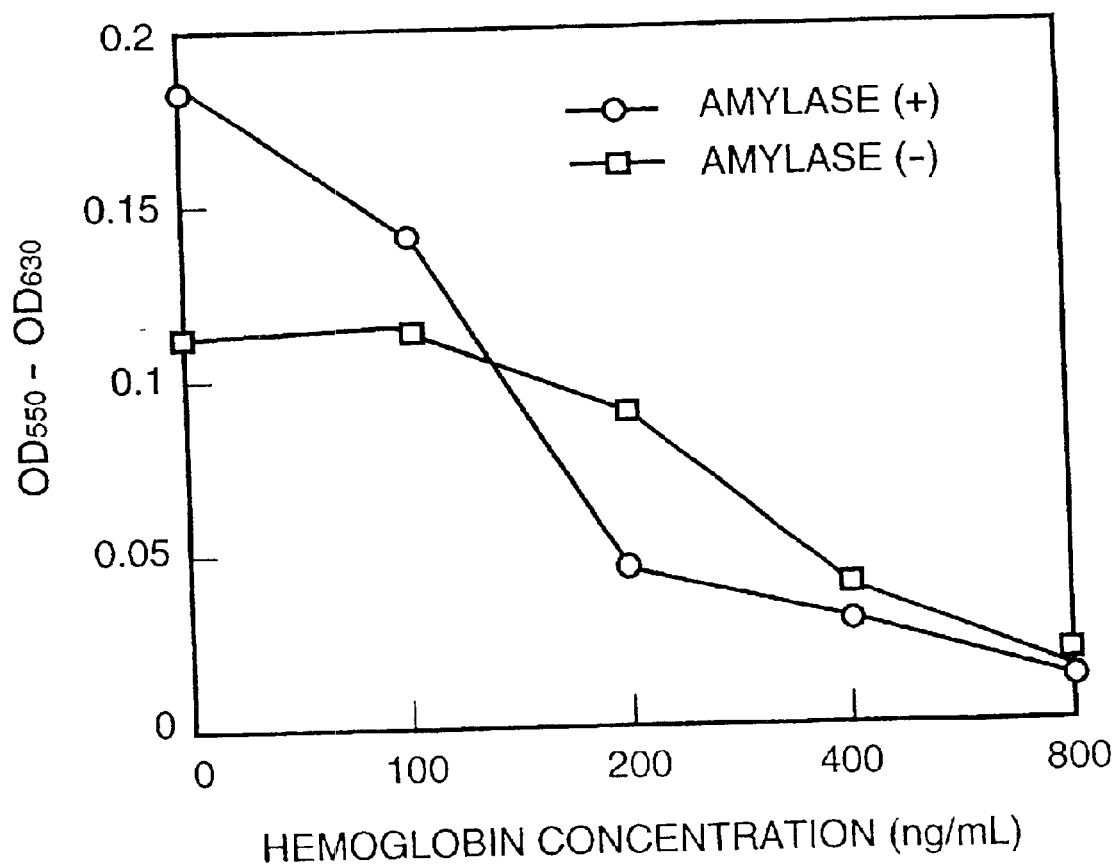
FIG. 2 is a graphic representation showing the results of Example 3, more specifically, calibration curves of dry analysis elements of the slide (1) obtained in example and slide (2) in comparative Example.

As illustrated in FIG. 2, compared with the comparative example slide (2) (-□- in the drawing), the slide (1) obtained in this example by using the cloth (water permeable layer) impregnated with α-amylase exhibited a larger difference in reflection optical density ($OD_{550}$–$OD_{630}$) relative to a change in the concentration of hemoglobin in a sample and therefore was superior in an S/N ratio (-○- in the drawing). Moreover, in the slide of comparative example, the optical density difference ($OD_{550}$–$OD_{630}$) in a range of the hemoglobin concentration not greater than 200 ng/mL was markedly small, while in the slide of this example, the difference was large, indicating that the analysis can be conducted with good sensitivity particularly in a low-concentration range.

According to the present invention, as described above, a non-fluid substance which has fluidity enhanced or grown up by a solation agent upon analysis is used as a medium to be a reaction place where the agglutination reaction takes place. Addition of the solation agent increases the fluidity of the non-fluid substance, thereby the particles bearing an anti-analyte can diffuse in the medium to cause the agglutination with an analyte. By mixing the particle bearing anti-analyte with the non-fluid substance to form a medium, the particle bearing anti-analyte (i.e., particle-labeled anti-analyte) can be dried in form of a dried medium enough not to damage the stability of a reagent composition upon storage. Upon analysis, medium is solated and liquefied by a solation agent, and fluidity enough for causing agglutination of the labeling particles can be ensured. As a result, an analyte can be analyzed by a dry analysis method.

The dry analysis element according to the present invention comprises a non-fluid medium layer for retaining a labeling particle having the anti-analyte; and a water permeable layer which contains a solation agent and is superimposed on the medium layer. Such a constitution makes it possible to cause agglutination in the medium layer, thereby carrying out convenient and highly-sensitive dry analysis of an analyte only by spotting and feeding a sample containing the analyte onto the water permeable layer.

What is claimed is:

1. An agglutination assay method for quantitative determination of an analyte in an aqueous liquid sample using particles bearing an anti-analyte, the anti-analyte being capable of specifically binding to the analyte so as to cause agglutination of the particles, comprising:

providing a mixture of said particles and a non-fluid substance which retains said particles while suppressing the diffusion of said particles;

contacting said mixture with a solation agent for increasing the fluidity of the non-fluid substance in said mixture;

contacting the sample with said mixture to cause the agglutination of the particles in said mixture; and measuring the extent of the agglutination of the particles to determine the amount of the analyte in the sample.

2. The method according to claim 1, wherein said solation agent is supplied to said mixture together with the sample.

3. The method according to claim 1, wherein said mixture constitutes a film, and wherein said solation agent and the sample are applied to the film, and the agglutination caused in the film is detected.

4. The method according to claim 1, wherein said mixture constitutes a film superimposed on a water permeable layer containing said solation agent, and wherein the sample is applied to the water permeable layer so that the sample is transferred to the film together with said solation agent.

5. The method according to claim 1, wherein said particles are latex particles.

6. The method according to claim 1, wherein said particles are colloidal metal and the degree of the agglutination of the particles is detected from a change in color tone of the colloidal metals caused by the agglutination.

7. The method according to claim 6, wherein said particles are colloidal gold or colloidal silver.

8. The method according to claim 1, wherein said non-fluid substance is a saccharide and said solation agent is a glucosidase.

9. The method according to claim 1, wherein said non-fluid substance is a polysaccharide and said solation agent is a glucosidase.

10. The method according to claim 9, wherein said polysaccharide is a starch derivative.

11. The method according to claim 1, wherein said analyte is an antigen and said anti-analyte is an antibody.

* * * * *